United States Patent
Joeken (10) Patent No.: US 8,556,818 B2
(45) Date of Patent: Oct. 15, 2013

(54) APPARATUS AND METHOD FOR DETERMINING A PHYSIOLOGIC PARAMETER OF A PATIENT APPLYING FOURIER TRANSFORMATION

(75) Inventor: Stephan Joeken, Schopfheim (DE)

(73) Assignee: Pulsion Medical Systems SE, Feldkirchen (DE)

( * ) Notice: Subject to any disclaimer, the term of this patent is extended or adjusted under 35 U.S.C. 154(b) by 1411 days.

(21) Appl. No.: 11/880,633

(22) Filed: Jul. 23, 2007

(65) Prior Publication Data

US 2008/0033306 A1   Feb. 7, 2008

(30) Foreign Application Priority Data

Aug. 3, 2006   (EP) ..................................... 06118387

(51) Int. Cl.
*A61B 5/08*   (2006.01)

(52) U.S. Cl.
USPC .......................................... 600/484; 600/485

(58) Field of Classification Search
USPC .......................................... 600/300, 481–507
See application file for complete search history.

(56) References Cited

U.S. PATENT DOCUMENTS

| | | | |
|---|---|---|---|
| 4,832,038 A * | 5/1989 | Arai et al. | 600/483 |
| 5,769,082 A * | 6/1998 | Perel | 600/484 |
| 6,315,735 B1 | 11/2001 | Joeken et al. | |
| 6,776,764 B2 | 8/2004 | Pinsky | |
| 7,740,591 B1 * | 6/2010 | Starr et al. | 600/534 |
| 2003/0033094 A1 * | 2/2003 | Huang | 702/39 |
| 2005/0124903 A1 * | 6/2005 | Roteliuk et al. | 600/526 |
| 2006/0195035 A1 * | 8/2006 | Sun | 600/503 |
| 2007/0021673 A1 * | 1/2007 | Arbel et al. | 600/500 |

FOREIGN PATENT DOCUMENTS

| | | |
|---|---|---|
| EP | 0 666 056 A1 | 8/1995 |
| EP | 0 947 941 A2 | 10/1999 |
| EP | 1 421 897 A1 | 5/2004 |
| WO | WO 99/02086 | 1/1999 |
| WO | 2005/069740 | 8/2005 |

OTHER PUBLICATIONS

Omboni, et al. "Spectral and sequence analysis of finger blood pressure variability. Comparison with analysis of intra-arterial recordings" 1993, Hypertension. vol. 22, pp. 26-33.*

Mukkamala et al., "Continuous Cardiac Output Monitoring by Peripheral Blood Pressure Waveform Analysis," Mar. 2006, IEEE Tran. Biomed. Eng., vol. 53, No. 3, pp. 459-467.*

Michard, "Volume Management Using Dynamic Parameters the Good, the Bad, and the Ugly" 2005, Chest, vol. 128, pp. 1902-1903.*

(Continued)

*Primary Examiner* — Patricia Mallari
*Assistant Examiner* — Eric Messersmith
(74) *Attorney, Agent, or Firm* — Collard & Roe, P.C.

(57) ABSTRACT

The apparatus comprises a pressure sensor providing readings of a blood pressure of the patient and storage means for storing the readings as a pressure curve over time. Blood pressure is measured. The frequency difference between heart rate and breathing rate is used to separate the respiratory effect from the heart activity. In particular, the Fourier transform of the blood pressure and the spectral density are used to determine the contribution of each frequency. The respiratory and cardiac power spectra are determined. The ratio between both powers is calculated as the quotient of the integrals over the cardiac power spectrum and the respiratory power spectrum. A parameter usable to characterize volume responsiveness is determined using above ratio and a correction factor.

21 Claims, 5 Drawing Sheets

(56) References Cited

OTHER PUBLICATIONS

Michard, Fréd, and Teboul, Jean-Louis, "Predicting Fluid Responsiveness in ICU Patients", Chest 121 (2002), pp. 2000-2008.
Reuter, D.A., et al., "Optimizing fluid therapy in mechanically ventilated patients after cardiac surgery by on-line monitoring of left ventricular stroke volume variations. Comparison with aortic systolic pressure variations", Br. J. Anaesth. 88 (2002), pp. 124-126.
Teboul, Jean-Louis, "What is the best way to assess fluid responsiveness in a spontaneously breathing patient?", Haemodynamic monitoring in shock and implications for management, 8th International Consensus Conference (2005).

\* cited by examiner

APPARATUS AND METHOD FOR DETERMINING A PHYSIOLOGIC PARAMETER OF A PATIENT APPLYING FOURIER TRANSFORMATION

The present invention relates to an apparatus for determining a physiologic parameter of a patient. In particular, the invention relates to an apparatus for determining at least one physiologic parameter of a patient which comprises at least one pressure sensor device adapted to provide readings of a blood pressure of the patient and storage means for storing said readings as at least one pressure curve over time.

Furthermore, the invention also relates to a method of determining at least one physiologic parameter of a patient providing readings of a blood pressure of the patient and storing said readings as at least one pressure curve over time.

Apparatus and methods of the type initially mentioned are well-known from the prior art and widely used in bedside monitoring of critically ill patients. Beside simple applications wherein the only physiologic parameter to be determined is the blood pressure itself, a pulse contour analysis is usually performed to determine various physiologic, more particular hemo-dynamic, parameters from the (temporarily) stored pressure curve. EP 0 947 941 A2, for example, describes in-vivo determination of the compliance function and the cardiac output of a patient using pulse contour analysis.

Cardiac output is among the most important parameters determined in bedside monitors. By definition, cardiac output (CO) is equal to the stroke volume multiplied by the heart rate (HR). The three principal factors affecting stroke volume are preload, afterload and myocardial contractility. A common definition of preload is the volume of blood that remains in the left ventricle at the end of the diastole, i.e. the left ventricular end diastolic volume (LVEDV). Generally, preload is a reflection of the volume status of a patient (i.e. the filling state of the patient's circulatory system), but it cannot be measured directly in clinical practice. Afterload is defined as impedance or resistance to ventricular contraction. Myocardial contractility is defined as the ability of the myocardial muscle to contract.

If cardiac output of a monitored patient is too low, the physician in charge will have to consider counter measures that may have to be taken. Generally, depending on the filling state of the circulatory system, and also on the individual patient, adding volume may have a significant or only little effect on cardiac output. A term frequently used to describe this behavior is volume responsiveness. In clinical practice often blood volume is increased and the reaction of the patient organism is observed. However, adding volume may involve the risk of creating a pulmonary edema.

Therefore, there has been a considerable endeavor to determine parameters helping the physician in charge to correctly assess volume-responsiveness, i.e. to assess whether the cardiovascular system will respond to adding fluid by an increased cardiac output (CO) and which CO will result.

Fréd Michard and Jean-Louis Teboul, *"Predicting fluid responsiveness in ICU patients"*, Chest 121(2002), 2000-2008 and D. A. Reuter et. al., *"Optimizing fluid therapy in mechanically ventilated patients after cardiac surgery by on-line monitoring of left ventricular stroke volume variations. Comparison with aortic systolic pressure variations. Br. J. Anaesth.* 88 (2002), 124-126 disclose using the parameters stroke volume variation (SVV) and pulse pressure variation (PPV) for determining volume-responsiveness of a patient. However, this approach is limited to controlled mechanically ventilated patient and cannot be applied to spontaneously breathing patients.

U.S. Pat. No. 6,776,764 B2 discloses a treatment algorithm for managing hemodynamically unstable patients by means of calculated pulse pressure variation (PPV) or stroke volume variation (SVV). Depending on the patient's state, volume management, vasopressor management or inotropic and cardiac management are suggested. However, due to the common limitations of PPV and SVV measurement, this approach can be used for controlled ventilated patients only.

EP 0 666 056 A1 discloses the so-called respiratory variation test (RSVT), according to which tidal volume or ventilation pressure are varied during one or more breathing cycles and a hemodynamic parameter is determined under these varying conditions. It is evident that this approach is also limited to controlled mechanically ventilated patient.

For assessing volume-responsiveness of a spontaneously breathing patient, Jean-Louis Teboul, *"What is the best way to assess fluid responsiveness in a spontaneously breathing patient?"*, Haemodynamic monitoring in shock and implications for management, 8th International consensus conference (2006) suggests raising the legs of the patient in order to vary preload. However, depending on the particular circumstances, such as injuries of the monitored patient, mechanically raising the patient's legs in a defined manner may be difficult or virtually impossible.

Generally, when applying apparatus of the type initially mentioned, regardless of whether volume-responsiveness is to be determined, correct consideration of the ventilation state of the patient can be difficult to achieve. Due to superimposed cardiac and respiratory effects on pressure measurements common evaluation algorithms not always lead to results of satisfactory reliability.

It is therefore an object of the present invention to provide an apparatus of the type initially mentioned allowing to correctly account for the influence of the present breathing state of the patient. Further, it is an object of the present invention to allow applying an apparatus of the type initially mentioned for mechanically ventilated patients and spontaneously breathing patients alike. Under one aspect, it is a particular object of the invention to provide an apparatus of the type initially mentioned, wherein the determined physiological parameter improves assessment of volume-responsiveness of the patient, regardless whether the patient is mechanically ventilated or spontaneously breathing.

Likewise, it is an object of the present invention to provide a method of the type initially mentioned allowing to correctly account for the influence of the present breathing state of the patient. Further, it is an object of the present invention to allow applying a method of the type initially mentioned for mechanically ventilated patients and spontaneously breathing patients alike. Under one aspect, it is a particular object of the invention to provide a method of the type initially mentioned, wherein the determined physiological parameter improves assessment of volume-responsiveness of the patient, regardless whether the patient is mechanically ventilated or spontaneously breathing.

The apparatus and method of the present invention provide reliable parameter determination from the variation in time of blood pressure readings retrieved by employing one or more invasively or non-invasively applied pressure sensors.

Therein, the present invention uniquely exploits the frequency difference between heart rate and breathing rate in order to separate the respiratory effect from the heart activity. In particular the Fourier transform of a blood pressure and the spectral density (Fourier transform of the autocorrelation function) are used to determine the contribution of each frequency: In the received power spectrum, the peaks caused by the respiratory rate and higher harmonics can be separated from the peaks caused by the heart rate and higher harmonics. Therefore, a respiratory power spectrum and a cardiac power spectrum, respectively, are retrieved. (In order to implement the present invention, it is not necessary to literally store separate respiratory and cardiac power spectra, but evaluation may also be performed upon the joint power spectrum, i.e. the superposition of the two spectra, considering only the peaks resulting from either heart rate or respiratory heart rate, respectively, depending on which parameter is to be determined.)

By integrating over at least part of cardiac or respiratory power spectrum, a cardiac or respiratory power value, respectively, is received. (Instead of an actual integration a method delivering a suitable approximation of an integration may be used.) One or both power values are then used for determining the physiological parameter (or parameters) of interest. For example, cardiac output may be calculated as the cardiac power value divided by an averaged blood pressure, possibly employing a suitable correction function. According to a particularly preferred embodiment of the present invention a parameter usable for assessing volume-responsiveness is calculated as the quotient of the cardiac power-value (i.e. the power value determined from the cardiac power spectrum) and the respiratory power-value (i.e. the power value determined from the respiratory power spectrum), possibly employing a suitable correction function.

The present invention is applicable to spontaneously breathing living beings as well as to patients with assisted breathing or fully controlled ventilated patients. Moreover, if volume-responsiveness is to be determined, no additional effort is necessary (such as leg raising maneuver, fluid or drug delivery), so that responsiveness can be determined in clinical practice by making use of the approach described herein.

Generally, any of the embodiments described or options mentioned herein may be particularly advantageous depending on the actual conditions of application. Further, features of one embodiment may be combined with features of another embodiment as well as features known per se from the prior art as far as technically possible and unless indicated otherwise. In particular, the apparatus and method of the present invention can be combined with conventional pulse contour analysis, as the pressure signal may be used for both the conventional pulse contour approach and the approach described herein.

The invention will now be described in more detail. The accompanying drawings, which are schematic illustrations, serve for a better understanding of the features of the present invention. Therein

In the drawings, the same reference numerals have been used for corresponding features.

Figure 1:
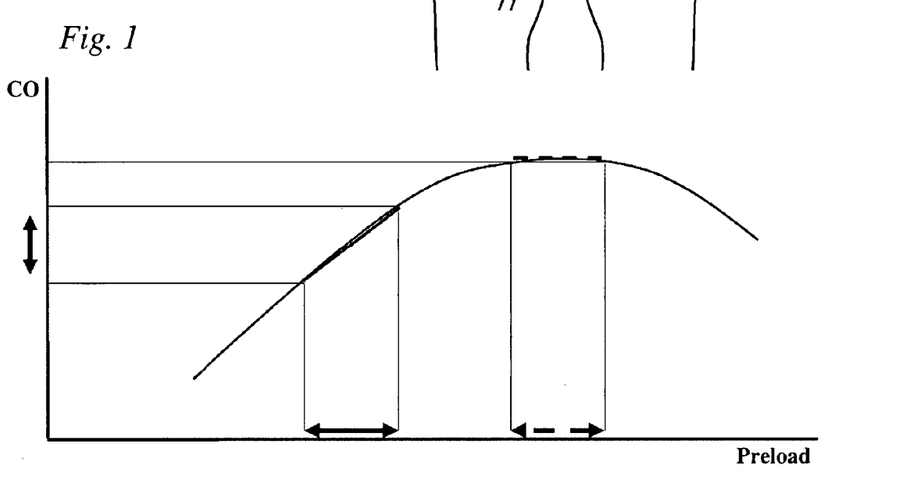
FIG. 1 is a diagram illustrating the concept of volume-responsiveness by showing a typical graph of cardiac output over preload.

Though the embodiments described below focus on determining a parameter usable to characterize volume responsiveness, other physiologic parameters (such as cardiac output or tidal volume) may also (or alternatively) be determined. However, the apparatus and method according to the present invention are particularly advantageous for determining a parameter usable to characterize volume responsiveness. In order to illustrate the above-mentioned fact that an increase of blood volume (or preload) does not necessarily raise cardiac output, FIG. 1 shows a typical graph of cardiac output depending on preload (or blood volume). The graph varies from patient to patient (and depends on the individual patient's current condition). Depending on the local slope, additional volume may greatly increase (curve section marked with solid line) or not increase (curve section marked with dashed line) cardiac output. As the actual course of the curve schematically shown in FIG. 1 is not known beforehand for a specific patient in a specific condition, acquiring parameters helping to assess volume responsiveness can be crucial in clinical practice.

Figure 7:
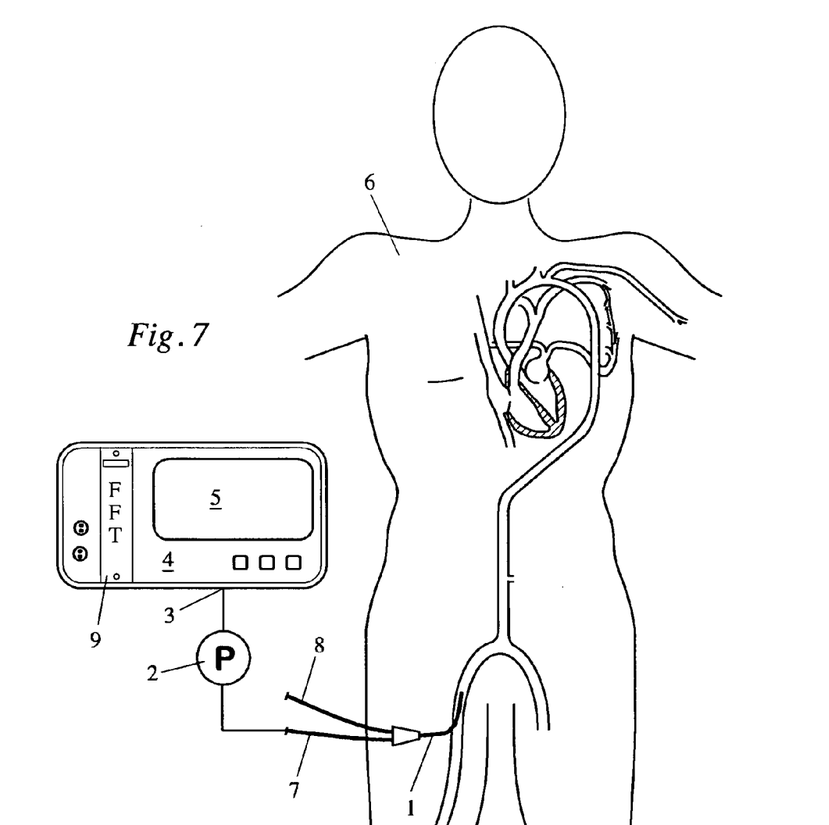
FIG. 7 illustrates the general setup of an apparatus according to a first embodiment of the present invention.

FIG. 7 shows the general setup of an apparatus according to a first embodiment of the present invention. An arterial catheter 1 is equipped with a pressure sensor for measuring arterial blood pressure. The pressure sensor of the catheter 1 is connected, via a pressure transducer 2, to an input channel 3 of a patient monitoring apparatus 4. Beside a proximal port 7 used to acquire the pressure signal, the catheter 1 may comprise one or more other proximal ports 8 to perform additional functions, such as blood temperature measurements or the like. The patient monitoring apparatus 4 is programmed to determine various hemodynamic parameters as described below, and to display the determined parameters (as numeric values, graphically or both) on the display 5. In addition, the determined parameters may be stored at a recording medium and/or printed. For this purpose, the patient monitoring apparatus 4 may comprise various interface ports for connecting peripheral equipment.

This first embodiment described requires a single arterial pressure sensor only. Though the sensor is shown to be invasive, a non-invasive pressure sensor may be implemented instead.

Various implementations of the invasive pressure sensor can be particularly advantageous. Pressure can either be transmitted hydraulically to a proximal catheter port and measured by an external sensor or may be measured directly on-site using a sensor installed at or near the catheter tip. Capacitative sensors, piezo sensors or optical pressure sensors (e.g. based on Fabry-Perot interferometry) may be used.

Figure 2:
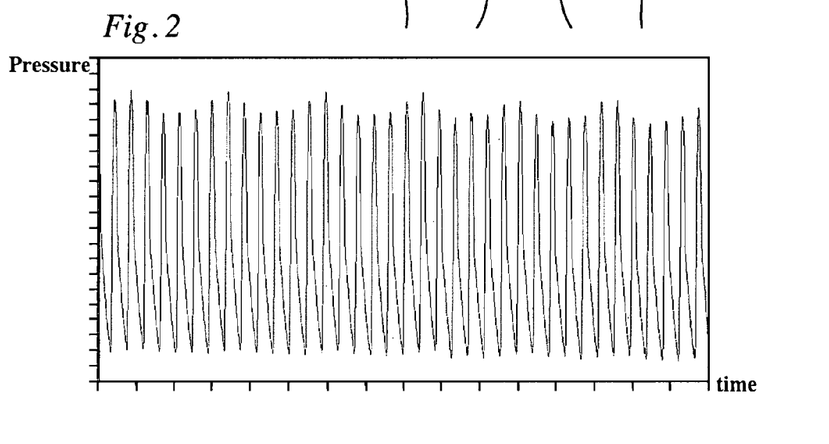
FIG. 2 is a typical plot of arterial pressure readings over time illustrating the effect of breathing on arterial pressure.

As explained above, cardiac, vasculary and pulmonary volumes interact with each other in the patient 6. In particular, cardiac preload is affected by the volume occupied by respiration (either spontaneous or ventilated breathing). Due to recurrent respiratory cycles modulation of blood pressure and flow take place. FIG. 2 shows this modulation in a typical plot of arterial pressure readings over time. Such a modulation can also be observed for central venous pressure or stroke volume.

The patient monitoring apparatus 4 temporarily stores the blood pressure readings read in through the input channel 3 as a pressure curve p(t) over time. As heart rate and breathing cycle differ in frequency (f), the respiratory effect on the pressure curve can be separated from the heart activity. The patient monitoring apparatus 4 thus determines breathing cycle and heart rate from the pressure signal.

In particular, the patient monitoring apparatus 4 contains fast Fourier transformation means (FFT) 9 in order to perform a Fourier transformation on the stored pressure curve. The Fourier transform of the blood pressure p(t) and the spectral density $S(\omega)$, i.e. the Fourier transform of the autocorrelation function, which is also determined by the FFT, are used to determine the contribution of each frequency $f=\omega/2\pi$ for further evaluation.

Figure 4:
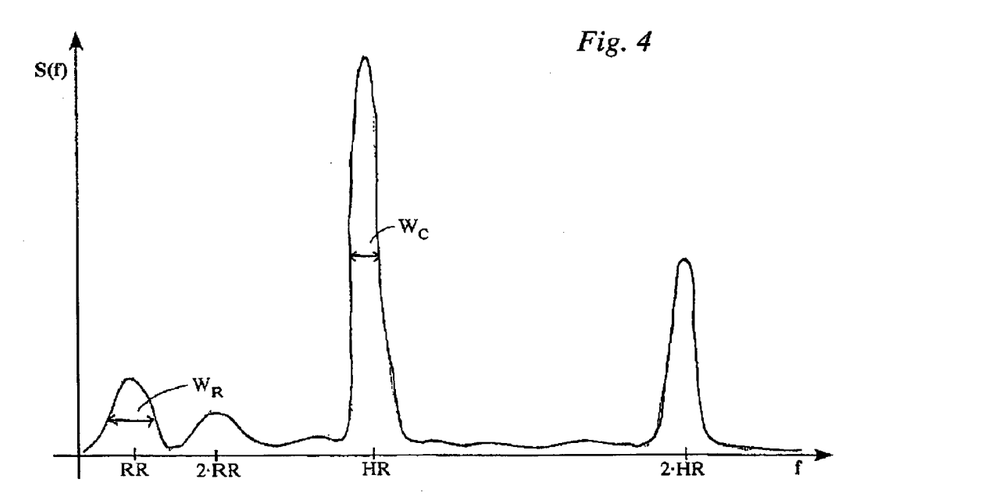
FIG. 4 shows a typical power spectrum based on readings of arterial pressure.
Figure 5:
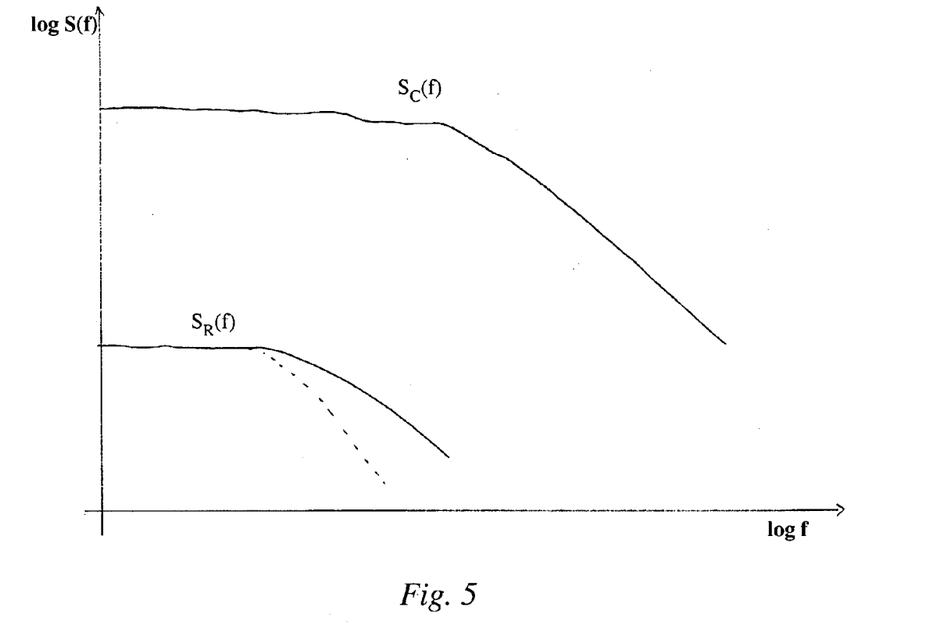
FIG. 5 shows the power spectra of heart activity and respiratory effects in double logarithmic scaling wherein the curves have been smoothed to illustrate the general course of the curve.
Figure 9:
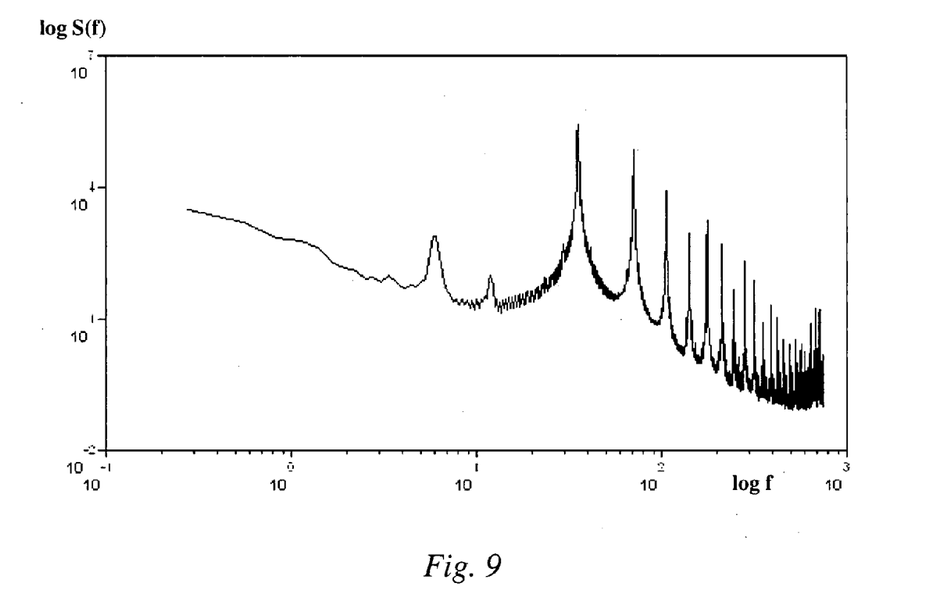
FIG. 9 shows a power spectrum in double logarithmic scaling, wherein the contributions of heart activity and respiratory have not been separated.

A power spectrum, i.e. the spectral density S in dependence of the frequency f, of an arterial blood pressure measurement is shown in FIG. 4. From the spectral density of the pressure signal the components (visualized as "peaks") caused by the respiratory rate (RR) and higher harmonics, i.e. 2·RR, 3·RR, . . . , can be separated in the power spectrum, as mentioned above. The components caused by the heart rate (HR) and higher harmonics, i.e. 2·HR, 3·HR, . . . , can also be separated in the power spectrum. Therefore, both the power spectrum $S_R(f)$ caused by respiration and the spectrum $S_C(f)$ caused by heart activity can be determined from the pressure measurements. For illustration, FIG. 5 shows the power spectrum of heart activity $S_C(f)$ and respiratory components $S_R(f)$ in dependence of the frequency f with logarithmic scaling on both axis. The solid line illustrates the behavior of spectral density of a ventilated patient 6 in comparison with a spontaneously breathing patient 6 (dashed line). For illustration purposes only, the curves have been smoothed. FIG. 9 shows, in comparison, a realistic power spectrum in double logarithmic scale, wherein the curve has not been smoothed. In FIG. 9, cardiac and respiratory contributions to the curve have not been separated.

In particular, the patient monitoring apparatus 4 determines in the spectral density of the pressure signal the magnitudes for the respiration rate and higher harmonics thereof, which leads to the respiratory power spectrum. Likewise, the cardiac power spectrum is determined from the amplitudes in the spectral density at the heart rate and higher harmonics thereof. A width at a predetermined fraction of the maximum of a respective peak (such as the full width at half maximum $W_R$ and $W_C$, as depicted in FIG. 4) may or may not be used to separate harmonics and to determine the amount of each.

Integration of the spectral densities over the whole frequency range permits determination of a respiratory power corresponding to respiration and a cardiac power corresponding to heart activity. However, integration over only part of the frequency range will in many cases lead to sufficient approximations or even improve the quality of the results: While the integrals have to run over a suitable range, several frequencies may be suppressed to reduce or eliminate signal disturbances.

The thus determined respiratory and cardiac power values can now be used by the patient monitoring apparatus 4 to calculate the hemodynamic parameters of interest and display the determined parameters on the display 5.

For example, the ratio of respiratory and cardiac power is used as a parameter to assess volume responsiveness (FR) according to $$FR=\int S_C(f)df / \int S_R(f)df$$

and cardiac output may be calculated as the cardiac power value divided by an averaged blood pressure.

Figure 8:
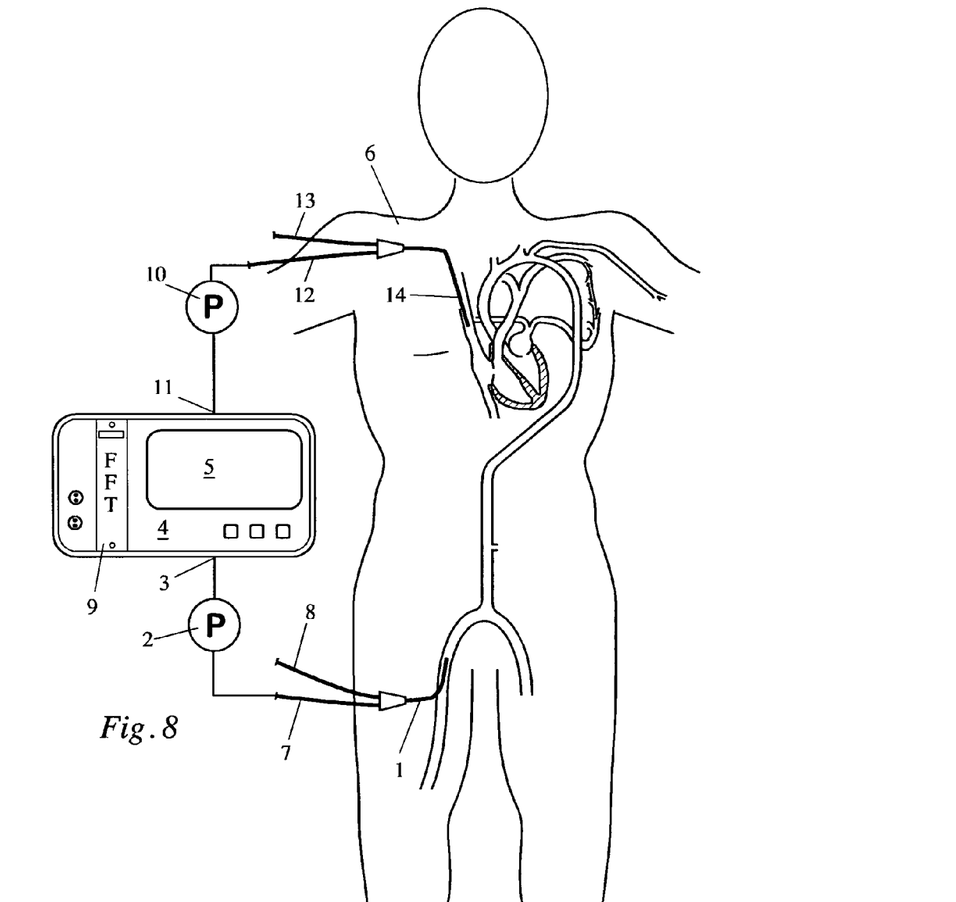
FIG. 8 illustrates the general setup of an apparatus according to another embodiment of the present invention.

FIG. 8 shows the general setup of an apparatus according to the second embodiment, wherein two pressure sensors are used. In addition to the arterial pressure measured as described in connection with the above first embodiment, a central venous pressure (CVP) is measured using a pressure sensor in a central venous catheter 14. The pressure sensor of the central venous catheter 14 is connected, via a pressure transducer 10, to a second input channel 11 of the patient monitoring apparatus 4. Beside a proximal port 12 used to acquire the pressure signal, the catheter 14 may comprise one or more other proximal ports 13 to perform additional functions, such as blood temperature measurements, injections or the like. Instead of the central venus catheter 14 a pulmonary catheter (not shown) may be used to provide readings of a pulmonary pressure (PAP or PCWP). Generally, various measurement sites are suitable for providing first and second blood pressure readings.

Though one or both pressure sensors may also be non-invasive, as mentioned in connection with the first embodiment described above, best performance of the system can be achieved with two invasive pressure sensors, as depicted in FIG. 8.

As described above, various implementations of the invasive pressure sensors can be particularly advantageous. Pressure can either be transmitted hydraulically to a proximal catheter port and measured by an external sensor or may be measured directly on-site using a sensor installed at or near the catheter tip. Capacitative sensors, piezo sensors or optical pressure sensors (e.g. based on Fabry-Perot interferometry) may be used.

Figure 3:
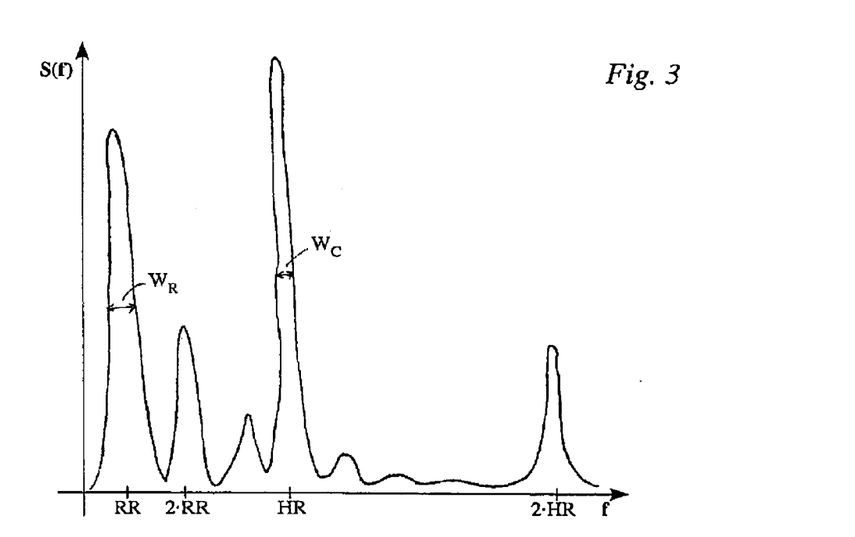
FIG. 3 shows a typical power spectrum based on readings of central venous pressure.

The patient monitoring apparatus 4 determines the breathing cycle from the central venous pressure signal. Using the fast Fourier transformator (FFT) 9, the patient monitoring apparatus 4 determines the spectral density, which is shown in an exemplary manner in FIG. 3. In the spectral density derived from this pressure signal, the magnitudes are determined for the respiration rate and higher harmonics thereof, which leads to the respiratory power spectrum. A width at a predetermined fraction of the maximum of a respective peak (such as the full width at half maximum $W_R$ and $W_C$, as depicted in FIG. 3) may or may not be used to separate harmonics and to determine the amount of each. Summation/integration over (at least part of) the respiratory power spectrum delivers the respiratory power.

The heart rate is determined from the arterial pressure signal. The cardiac power spectrum is determined from the amplitudes in the spectral density at the heart rate and higher harmonics thereof. A width at a predetermined fraction of the maximum of a respective peak (such as the full width at half maximum $W_R$ and $W_C$, as depicted in FIG. 4) may or may not be used to separate harmonics and to determine the amount of each. Cardiac power is determined by summation/integration over (at least part of) the cardiac power spectrum.

Finally, the ratio of respiratory and cardiac power is provided as a measure of volume responsiveness as described above in connection with the first embodiment.

Further improvements of either of above-described embodiments include the following:

The power spectra can be characterized with respect to the kind of breathing (mechanically ventilated or spontaneous). In particular the full width at half maximum $W_R$ (see FIGS. 3 and 4) or other width at a predetermined fraction of the maximum of a respective peak, the slope of log $S_R(f)$ over log f for f approaching infinity (see FIG. 5), the slope of log $S_C(f)$ over log f for f approaching infinity (see FIG. 5), the limits $\lim_{f \to 0} S(f)$, $\lim_{f \to 0} S_R(f)$ and $\lim_{f \to 0} S_C(f)$ are of special interest.

Controlled ventilation typically differs from spontaneous breathing by a smaller full width at half maximum $W_R$ and a slower decrease of log $S_R(f)$ with respect of log f at higher frequencies (see FIG. 5). As sensitivity of the approach according to the present invention may differ depending on spontaneous breathing and controlled ventilation, respectively, the volume responsiveness parameter FR can be corrected by a factor κ:

$$FR = \kappa(W_R, a_R, \ldots) \cdot \int S_C(f) df / \int S_R(f) df$$

wherein $a_R$ denotes the slope of log $S_R(f)$ over log f at higher frequencies.

Both, $a_R$ and $a_C$ (the slope of log $S_C(f)$ over log f at higher frequencies), can be used to extend the integrations $\int S_C(f) df$ and $\int S_R(f) df$, respectively. Therefore, calculation of the ratios become more precise. Precision can also be improved by taking into account limits of spectra for f approaching 0. However, for most cases using the spectral density for f=0 is not recommended, as these values consider offsets in the pressure measurements only.

In addition, external input (e.g. by means of an interface to a ventilation machine or by user input determining the kind of current respiration) may be used to support determination of the correction factor κ.

Figure 6:
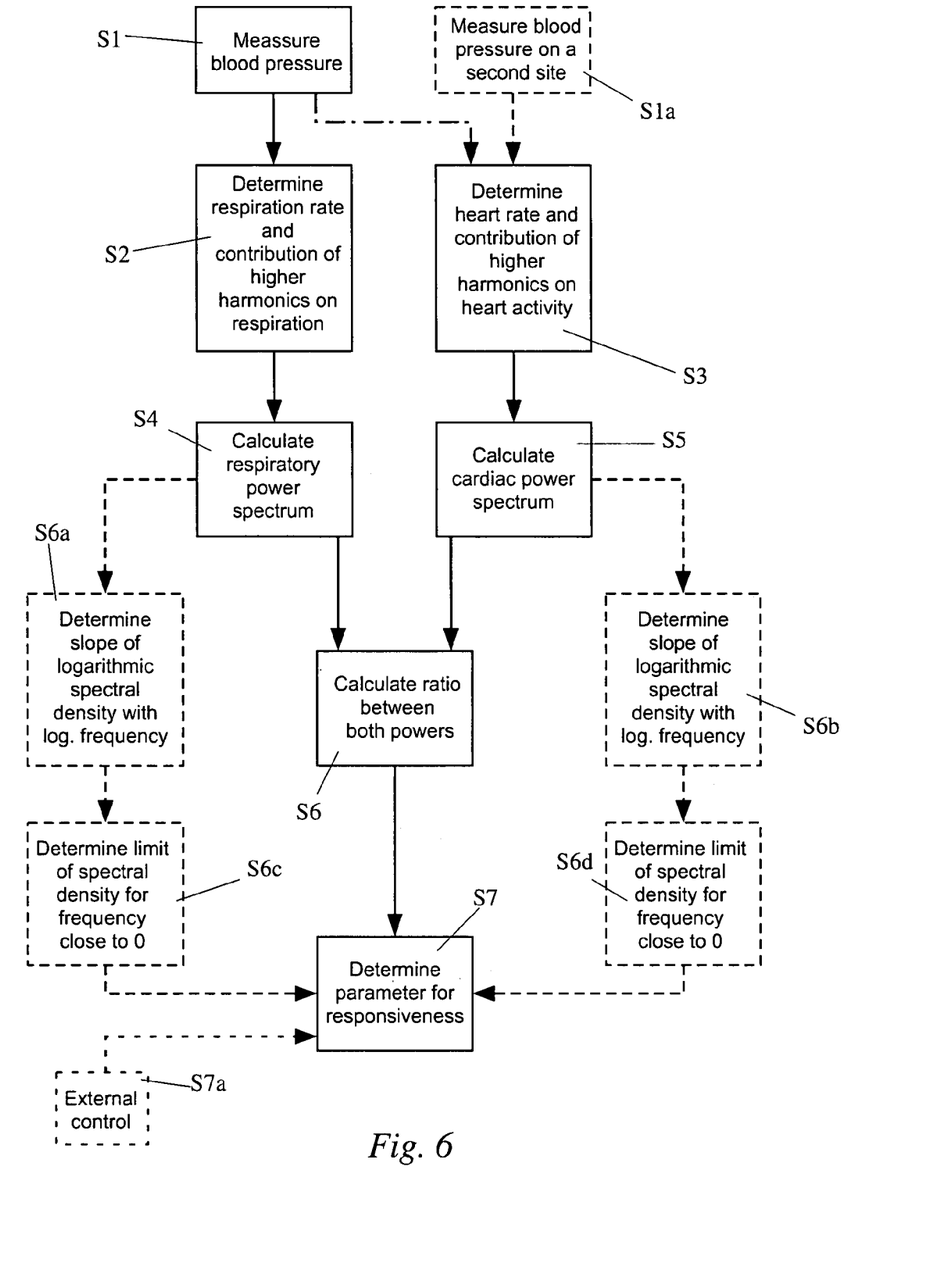
FIG. 6 shows a flow sheet of determining volume-responsiveness according to one embodiment of the present invention, wherein several options are illustrated using dashed lines.

For a better understanding of the above, FIG. 6 shows an overview of method steps according to embodiments of the present invention adapted to determine a parameter for volume responsiveness as described above or similar. The method steps may be performed by the above described apparatus or otherwise. Dashed lines show an alternative embodiment including several options added to the basic embodiment (solid lines).

Blood pressure is measured (S1), optionally also at a second site (S1a). As described above, the respiration rate and the contribution of higher harmonics on respiration are determined (S2), as well as the heart rate and the contribution of higher harmonics on heart activity (S3). The respiratory and cardiac power spectra are determined (S4, S5). The ratio between both powers is calculated as the quotient of the integrals over the cardiac power spectrum (enumerator) and the respiratory power spectrum (denominator) (S6). The parameter usable to characterize volume responsiveness is determined (S7) and displayed or otherwise output. Determining this parameter may simply be acquiring the above ratio between cardiac and respiratory power or it may involve a correction factor (or a more complex correction function) using determination of the slopes of logarithmic spectral densities over logarithmic frequency (S6a, S6b), see also FIG. 5, and/or determination of the spectral density for frequency approaching zero (S6c, S6d). Further (or alternatively) correction may be achieved by external control (S7a).

The invention claimed is:

1. Apparatus for determining at least one physiologic parameter of a patient, said apparatus comprising
   (a) at least one pressure sensor device adapted to provide readings of a blood pressure of said patient, and
   (b) storage means for storing said readings as at least one pressure curve over time,
   (c) fourier transformation means for subjecting said at least one pressure curve to a fourier transformation, and
   (d) an evaluator adapted to retrieve at least one power value selected from a group consisting of
      a cardiac power value representing cardiac power and
      a respiratory power value representing respiratory power from at least one fourier transform received from said fourier transformation means and to determine said physiologic parameter from said at least one power value,
   wherein said evaluator is adapted to extract at least one power-spectrum selected from the group consisting of
      a cardiac power-spectrum and
      a respiratory power-spectrum;
   from at least one fourier transform received from said fourier transform means to determine a width at a predetermined fraction of the maximum of a peak of said at least one power-spectrum and to use said width to separate harmonics.

2. Apparatus according to claim 1, wherein said evaluator is adapted to separate said harmonics using at least one of a heart rate and a breathing rate as a basic frequency.

3. Apparatus according to claim 1, wherein said evaluator is adapted to determine at least one of
   said cardiac power value using summation over at least part of said cardiac power-spectrum
   said cardiac power value using integration over at least part of said cardiac power-spectrum
   said respiratory power value using summation over at least part of said respiratory power-spectrum
   said respiratory power value using integration over at least part of said respiratory power-spectrum.

4. Apparatus according to claim 1, wherein said evaluator is adapted to use said width to determine the amount of said harmonics from at least one of said cardiac power-spectrum and said respiratory power-spectrum.

5. Apparatus according to claim 1, wherein said evaluator is adapted to determine both said cardiac power-value and said respiratory power-value from a fourier transform received from said fourier transformation based on the same pressure curve.

6. Apparatus according to claim 1 comprising at least two pressure sensor devices adapted to provide readings of a blood pressure of said patient,
   wherein the apparatus is adapted to store readings of a first one of said pressure sensor devices as a first pressure curve over time and readings of a second one of said pressure sensor devices as a second pressure curve over time,
   and wherein said evaluation means are adapted to determine said cardiac power-value from a fourier transform received from said fourier transformation based on said first pressure curve and said respiratory power-value from a fourier transform received from said fourier transformation based on said second pressure curve.

7. Apparatus according to claim 6, wherein said first pressure sensor device is an arterial pressure sensor device and said second pressure device is one of a central venous pressure device and a pulmonary artery pressure device.

8. Apparatus according to claim 6, wherein said evaluation means are adapted to determine cardiac output from the quotient of said cardiac power-value and an averaged pressure calculated from said readings of a blood pressure of said patient.

9. Apparatus according to claim 1, further comprising at least one pressure sensor device adapted for non-invasively measuring an arterial pressure of said patient.

10. Apparatus according to claim 1, wherein said at least one physiologic parameter of said patient includes cardiac output, and wherein said evaluator is adapted to determine cardiac output using said cardiac power-value.

11. Apparatus according to claim 1, wherein said evaluation means are adapted to determine at least one further hemodynamic parameter from said at least one pressure curve over time.

12. Apparatus for determining at least one physiologic parameter of a patient, said apparatus comprising
(a) at least one pressure sensor device adapted to provide readings of a blood pressure of said patient, and
(b) storage means for storing said readings as at least one pressure curve over time,
(c) fourier transformation means for subjecting said at least one pressure curve to a fourier transformation, and
(d) an evaluator adapted to retrieve at least one power value selected from a group consisting of
a cardiac power value representing cardiac power and
a respiratory power value representing respiratory power from at least one fourier transform received from said fourier transformation means and to determine said physiologic parameter from said at least one power value,
wherein said at least one physiologic parameter of the patient includes a parameter indicative of volume-responsiveness.

13. Apparatus according to claim 12, wherein said evaluator is adapted to retrieve both the cardiac power value and the respiratory power value and is adapted to determine said parameter for volume-responsiveness from the quotient of said cardiac power-value and said respiratory power-value.

14. Apparatus according to claim 12, wherein said evaluator is adapted to determine said parameter for volume-responsiveness using a correction factor.

15. Apparatus according to claim 14, wherein said evaluator is adapted to determine said parameter for volume-responsiveness to be a product of said correction factor and the quotient of said cardiac power-value and said respiratory power-value.

16. Apparatus according to claim 14, wherein said evaluator is adapted to determine a cardiac power-spectrum and a respiratory power spectrum from at least one fourier transform received from said fourier transformation, to determine said cardiac power value using summation or integration over at least part of said cardiac power-spectrum and said respiratory power value using summation or integration over at least part of said respiratory power-spectrum, and to determine at least one of the following characteristic parameters
a width (WC, WR) at a predetermined fraction of the maximum of a peak of said cardiac power-spectrum,
a slope of logarithmic spectral density of said cardiac power-spectrum over logarithmic frequency for frequency tending towards infinity,
a slope of logarithmic spectral density of said respiratory power-spectrum over logarithmic frequency for frequency tending towards infinity,
a limit of the spectral density of said cardiac power-spectrum tending towards zero,
a limit of the spectral density of said respiratory power-spectrum tending towards zero,
a limit of the spectral density of the superposition of said cardiac power-spectrum and said respiratory power-spectrum tending towards zero,
and wherein said correction factor is a function of at least one of said characteristic parameters.

17. Apparatus according to claim 12, wherein said evaluator is adapted to separate said harmonics using at least one of a heart rate and a breathing rate as a basic frequency.

18. Apparatus according to claim 12, wherein said evaluator is adapted to determine both said cardiac power-value and said respirator power-value from a fourier transform received from said fourier transformation based on the same pressure curve.

19. Apparatus according to claim 12, wherein at least one pressure sensor device is adapted for non-invasively measuring an arterial pressure of said patient.

20. Apparatus according to claim 12, wherein said at least one physiologic parameter of said patient includes cardiac output, and wherein said evaluator is adapted to determine cardiac output using said cardiac power-value.

21. Apparatus for determining at least one physiologic parameter of a patient, said apparatus comprising
(a) at least one pressure sensor device adapted to provide readings of a blood pressure of said patient, and
(b) storage means for storing said readings as at least one pressure curve over time,
(c) fourier transformation means for subjecting said at least one pressure curve to a fourier transformation, and
(d) an evaluator adapted to retrieve at least one power value selected from a group consisting of
a cardiac power value representing cardiac power and
a respiratory power value representing respiratory power from at least one fourier transform received from said fourier transformation means and to determine said physiologic parameter from said at least one power value,
wherein said at least one physiologic parameter of said patient includes tidal volume, and wherein said evaluation means are adapted to determine tidal volume using said respiratory power-value.

* * * * *